US009386766B2

(12) United States Patent
Cork

(10) Patent No.: US 9,386,766 B2
(45) Date of Patent: Jul. 12, 2016

(54) INSECT ATTRACTANT COMPOSITIONS

(75) Inventor: Alan Cork, London (GB)

(73) Assignee: University of Greenwich, London (GB)

( * ) Notice: Subject to any disclaimer, the term of this patent is extended or adjusted under 35 U.S.C. 154(b) by 77 days.

(21) Appl. No.: 13/501,564

(22) PCT Filed: Oct. 12, 2010

(86) PCT No.: PCT/GB2010/051716
§ 371 (c)(1),
(2), (4) Date: Apr. 12, 2012

(87) PCT Pub. No.: WO2011/045596
PCT Pub. Date: Apr. 21, 2011

(65) Prior Publication Data
US 2012/0207702 A1 Aug. 16, 2012

(30) Foreign Application Priority Data

Oct. 12, 2009 (GB) .................................. 0917781.7
Aug. 23, 2010 (GB) .................................. 1014038.2

(51) Int. Cl.
*A01N 35/04* (2006.01)
*A01N 35/02* (2006.01)
*A01N 37/40* (2006.01)
*A01N 49/00* (2006.01)

(52) U.S. Cl.
CPC .............. *A01N 35/04* (2013.01); *A01N 35/02* (2013.01); *A01N 37/40* (2013.01); *A01N 49/00* (2013.01)

(58) Field of Classification Search
None
See application file for complete search history.

(56) References Cited

U.S. PATENT DOCUMENTS

| 5,296,227 | A | | 3/1994 | Norval et al. |
| 5,885,600 | A | * | 3/1999 | Blum et al. .................... 424/405 |
| 6,074,634 | A | * | 6/2000 | Lopez et al. ..................... 424/84 |
| 6,190,652 | B1 | | 2/2001 | Pair et al. |
| 6,264,939 | B1 | * | 7/2001 | Light et al. ....................... 424/84 |
| 6,440,406 | B1 | | 8/2002 | Lopez, Jr. et al. |
| 6,849,614 | B1 | * | 2/2005 | Bessette et al. ................. 514/72 |
| 2005/0031661 | A1 | * | 2/2005 | Landolt et al. ................ 424/405 |
| 2005/0042316 | A1 | | 2/2005 | Gregg et al. |
| 2005/0147640 | A1 | * | 7/2005 | Sexton .......................... 424/410 |
| 2012/0207702 | A1 | | 8/2012 | Cork |

FOREIGN PATENT DOCUMENTS

| AU | 2008229734 | | 4/2010 |
| CN | 101268786 | * | 9/2008 |
| JP | 56087511 | | 7/1981 |
| WO | WO-98/27261 | * | 6/1998 |
| WO | WO-98/53678 | * | 12/1998 |
| WO | WO-00/19820 | * | 4/2000 |
| WO | WO-03/055308 | | 7/2003 |
| WO | WO-2005/020687 | | 3/2005 |

OTHER PUBLICATIONS

Deng et al. "EAG and behavioral responses of Helicoverpa armigera males to volatiles from polar leaves and their combinations with sex pheromone" 2004.*
Li et al. "Active compounds in *Populus nigra* L. wilted leaves responsible for attracting Helicoverpa armigera (Hubner) (Lep., Noctuidae) and new agaropectin formulation" (2005).*
Meagher et al. Attractiveness of binary blends of floral odorant compounds to moths in Florida 2008.*
Guo, et al., "Studies on the attraction to moths of volatile constituents of withered black poplar leaves", Journal of Henan Agricultural University, vol. 38, No. 3, Sep. 2004.
Huber, et al., "Angiosperm Bark Volatiles Disrupt Response of Douglas-Fir Beetle, *Dendroctonus pseudotsugae*, to Attractant-Baited Traps", Journal of Chemical Ecology, vol. 27, No. 2, 2001.
Li, et al., "Active compounds in *Populus nigra* L. wilted leaves responsible for attracting Helicoverpa armigera (Hübner) (Lep., Noctuidae) and new agaropectin formulation", Journal of Applied Entomology, vol. 129, No. 9, 2005.
Meagher, et al., "Attractiveness of binary blends of floral odorant compounds to moths in Florida, USA", Entomologia Experimentalis, vol. 128, No. 2, 2008.
T. J. Bruce et al., "Laboratory and field evaluation of floral odours from African marigold, *Tagetes erecta*, and sweet pea, *Lathyrus odoratus*, as kairomones for the cotton bollworm *Helicoverpa armigera*", in: Use of pheromones and other semiochemicals in integrated production, IOBC wprs Bulletin, vol. 25 (2002).
T.J. Bruce and A. Cork, "Electrophysiological and behavioral responses of female *Helicoverpa armigera* to compounds identified in flowers of African marigold, *Tagetes erecta*", Journal of Chemical Ecology, vol. 27, No. 6 (2001), pp. 1119-1131.
J.-Y. Deng et al., "EAG and behavioral responses of *Helicoverpa armigera* males to volatiles from poplar leaves and their combinations with sex pheromone", Journal of Zhejiang University Science, vol. 5, No. 12 (2004), pp. 1577-1582.
P.J. Landolt et al., "Moths trapped in Alaska with feeding attractant lures and the seasonal flight patterns of potential agricultural pests", The Canadian Entomologist, vol. 139 (2007), pp. 278-291.

* cited by examiner

*Primary Examiner* — Robert A Wax
*Assistant Examiner* — Danah Al-Awadi
(74) *Attorney, Agent, or Firm* — Heslin, Rothenberg, Farley & Mesiti, P.C.

(57) ABSTRACT

An attractant composition suitable for attracting Lepidopterous insects, particularly *Helicoverpa armigera*, for use as an insect lure in a control method aimed at reducing pest damage to crops. The preferred attractant composition comprises phenylacetaldehyde, salicylaldehyde and at least one compound selected from the group comprising: methyl-2-methoxybenzoate, linalool and limonene.

15 Claims, No Drawings

INSECT ATTRACTANT COMPOSITIONS

CROSS REFERENCE TO RELATED APPLICATIONS

This application is the national phase application of international application no. PCT/GB2010/051716, filed Oct. 12, 2010, which claims priority to Great Britain application no. 1014038.2, filed Aug. 23, 2010, and Great Britain application no. 0917781.7, filed Oct. 12, 2009. The contents of the aforementioned applications are incorporated herein.

The present invention relates to insect attractant compositions and particularly to insect attractant compositions for attracting moth pest species, such as *Helicoverpa armigera*.

Most larvae of the insect order Lepidoptera are phytophagous, the Lepidopterous moth families Noctuidae and Pyralidae including some of the most economically-important pest species. The American cotton bollworm, *Helicoverpa armigera*, is a particularly significant polyphagous pest of legume and solanaceous crops, such as chickpea, pigeon pea, lablab bean and tomato. *H. armigera* has been recorded in the UK but is of greater economic importance in the countries of southern Europe, particularly Spain, where it attacks cotton and tomato crops. Traits such as high mobility of adults and the ability of each female moth to lay between 500 and 3,000 eggs on a host-plant, enable rapid growth and dispersal of *H. armigera* populations.

Insect pests can be controlled by a variety of techniques, each method having particular advantages and disadvantages. Insecticides are a common control method for reducing pest populations. However, non-selective insecticide use can result in resistance development amongst pest populations. For example, *H. armigera* has developed resistance to pyrethroid and endosulfan insecticides in Australia and the Indian sub-continent. Use of transgenic plants, which have resistance to a particular pest, is an alternative strategy for minimising insect-mediated crop damage. Transgenic cotton, for example, has been widely used in the USA, South America, India and China.

Other insect control methods include mating disruption and mass trapping. Chemical ecologists have focused on the identification and application of sex pheromones for insect detection, monitoring and control programmes (Witzgall et al., 2010). The specificity of pheromones, however, usually limits their use to situations where there is a single key pest species (due to the prohibitive costs associated with providing a solution for a species-complex). The sex pheromone of *H. armigera* has been characterised, but its value for control and population monitoring is minimal. Research has shown that control of *H. armigera* using pheromones to disrupt mating is ineffective because, although adult females will not mate within treatment areas, they may return later to lay their eggs within test areas (Chamberlain et al., 2000). There is some evidence to suggest that mass-trapping male moths using the female sex pheromone can have an effect on populations, but given the mobility of female moths, such an approach is unlikely to form the basis of a comprehensive control method.

Certain plant species have floral attractant properties that have been successfully exploited as trap crops for control of *H. armigera*. Adult Lepidoptera are attracted to, and feed on, floral nectar. They will usually select a particular plant species for oviposition, but they can select a broad range of flowering plants for feeding. Nocturnal insect species rely on floral odours in order to locate these food sources (Weisenborn and Baker, 1990; Gabel et al., 1992; Heath et al., 1992; Zhu et at, 1993; Dobson, 1994). Therefore, moth species are expected to respond to a broad range of floral odours. Both male and female adult moths, feed on nectar sources and so floral baits advantageously attract both sexes.

Diurnal changes in flowers, such as petal opening and closing, anthesis and the presentation of nectar, are co-ordinated with the release of floral scents (which act as synomones), and the activities of the insect pollinators (Bünning 1967, Hess 1983). Matile and Altenburger (1988) studied fragrances released from four plant species. They found pronounced diurnal changes in the composition of floral fragrances of species such as *Odontoglossum constrictum* and *Citrus medica*. *Hoya carnosa* and *Stephanotis floribunda* floral emissions were found to be primarily nocturnal. However, not only did the total quantity of material released vary over time, the relative composition also changed. In the case of *Stephanotis floribunda*, the maximum release of methyl benzoate and linalool occurred at midnight, while the maximum release of 1-nitro-2-phenylethane occurred at noon. Similarly, head-space analysis of floral odours emitted by honeysuckle, *Lonicera japonica*, showed that much of the odour was emitted in the middle of the night (Ikeda et al., 1994). The odour was found to consist of 150 compounds. However, it was primarily characterised by compounds found in jasmine—(Z)-jasmone, (Z)-jasmine lactone, (E)- and (Z)-methyl jasmonate and methyl epi jasmonate. Nocturnal scented flowers are predominately pollinated by moths and, indeed, *L. japonica* has long slender nectaries that are inaccessible to day-flying Hymenoptera.

Diurnal Lepidoptera are also known to be sensitive to airborne chemicals originating from oak sap and rotten fruits (Ilse, 1928, Miyakawa, 1976, Scherer and Klob, 1987). It is not clear how important these odours are, since sap and fruit lack the accompanying visual effects produced by flowers. In the case of the diurnal moth, *Zygaena*, feeding behaviour is stimulated by both visual and olfactory stimuli (Naumann et al., 1991), while for the small white butterfly, *Pieris rapae crucivora*, visits to flowers of *Ligustrum japonicum* are thought to be mediated by olfaction alone (Honda et al., 1998).

Preliminary studies carried out by the present inventors, seeking to identify the attractive volatile components of plant species, resulted in the identification of electrophysiologically-active compounds from marigold, *Tagetes erecta*. Subsequent wind tunnel bioassays confirmed that synthetic blends of these compounds were as attractive as the natural floral extracts (Bruce and Cork, 2001). However, field tests conducted in chickpea crops proved inconclusive since they resulted in low trap catches. Further studies on the volatiles of maize plants have identified phenylacetaldehyde as a strong attractant for female *Helicoverpa armigera* (Pawar et al., 1993). This compound is also found in many flowering plants and is present in at least one commercially available insect attractant (Magnet®).

Chinese farmers have traditionally used dried leaves of poplar trees to attract *Helicoverpa armigera*. In 2005, Li et al. demonstrated that leaf extracts of *Populus nigra* could attract *Helicoverpa armigera* in cotton crops. This study employed a lure including a basic five-component blend comprising aromatics without phenolics, and containing additional components all present in the steam distillate of the leaves of *P. nigra*. The blended components were mixed in the proportions found in the steam distillate. The results indicated that volatile components of wilted leaves of *P. nigra* can also attract *H. armigera* adults. However, the results of these tests are not entirely clear since several of the components in the blend have also been shown to act as repellents of *H. armigera* in certain crops.

Following considerable interest in the development of floral odour-baits for insect pests, Australia's Commonwealth Scientific and Industrial Research Organisation (CSIRO) scientists developed an insect attractant known commercially as Magnet®. This product is based on a blend of volatile plant compounds and an insecticide for controlling *H. armigera* on cotton. The insecticide contained in Magnet® adversely affects pollinators attracted to the odour bait and can kill natural pest enemies and parasitoids that are important for the control of other cotton pests. Magnet® has a short field life (around three days), which is disadvantageous when the attractant is used with long-duration crops, such as cotton. The Magnet® formulation is not water-fast and so it can be quickly washed away in areas with significant rainfall.

The present invention seeks to provide an attractant that overcomes at least some of the disadvantages of Magnet®. The present invention also seeks to provide a chemical attractant for use in the capture of economically-important moths, particularly Lepidopterous moth families Noctuidae and Pyralidae, which is environmentally friendly.

In its broadest aspect, the present invention provides an insect attractant composition comprising phenylacetaldehyde and salicylaldehyde.

The present invention also provides an attractant composition for attracting insects, the composition comprising: phenylacetaldehyde and salicylaldehyde; and excluding at least one of: benzaldehyde, benzyl alcohol, and phenylethyl alcohol.

In another aspect, there is provided an attractant composition for attracting insects, the composition comprising phenylacetaldehyde and salicylaldehyde, wherein phenylacetaldehyde comprises between 40 and 97% of the total weight of the composition. Preferably, salicylaldehyde comprises between 3 and 60% of the total weight of the composition.

According to the present invention, there is provided an attractant composition for attracting insects, the composition comprising phenylacetaldehyde, salicylaldehyde and at least one of: methyl-2-methoxybenzoate, linalool and limonene. Preferably, the composition comprises at least two of methyl-2-methoxybenzoate, linalool and limonene. Ideally, at least two of: methyl-2-methoxybenzoate, linalool and limonene, each comprise between 3 and 30% of the total weight of the composition.

In a preferred embodiment, the composition comprises phenylacetaldehyde, salicylaldehyde, methyl-2-methoxybenzoate, linalool and limonene. Preferably, the ratio of phenylacetaldehyde:salicylaldehyde:methyl-2-methoxybenzoate:linalool:limonene is approximately 50:20:10:10:10.

Suitably, the composition further comprises one or more compounds selected from the group comprising: benzaldehyde, benzyl alcohol, phenylethyl alcohol, anisyl alcohol, α-pinene, butyl salicylate (Z)-jasmone, methyl salicylate, diacetone (4-hydroxy-4-methyl-2-pentanone), (E)-myroxide, (Z)-b-ocimene, and (R)-(−)-piperitone.

Advantageously, the composition further comprises an antioxidant. Preferably, the antioxidant is at least one of: α-tocopherol, a related tocotrienol (vitamin E) and butylated hydroxytoluene. Suitably, the amount of the antioxidant is between 10% and 100% of the total weight of the composition, based on the amount of phenylacetaldehyde.

Optionally, the composition further comprises at least one of: a UV screener, preferably carbon black, and a UV absorber, preferably at least one of o-hydroxybenzophenones and benzotriazoles. Alternatively or additionally, the composition further comprises at least one carotenoid, preferably vitamin A.

In one embodiment, the composition further comprises one or more insecticides. Preferably, at least one insecticide has a vapour action. More preferably, at least one insecticide is a pyrethroid or dichlorvos. In another embodiment, the composition comprises an insect-specific microbial pesticide. Preferably, the microbial pesticide is at least one of: a virus (preferably nucleopolyhedrovirus), fungus (preferably *Metarhizium anisopliae, Beauveria bassiana*) and bacteria (preferably *Bacillus thuringiensis*).

Optionally, the composition comprises a Hymenoptera deterrent.

According to a further aspect of the present invention, there is provided a lure comprising an insect attractant composition as described above.

Another aspect of the present invention provides use of a composition as described above to trap Lepidoptera.

A further aspect of the present invention provides use of an attractant composition comprising phenylacetaldehyde to trap *Diaphania indica*. Preferably, the composition further comprises salicylaldehyde. More preferably, the attractant composition further comprises at least one of: methyl-2-methoxybenzoate, linalool and limonene.

The above and other aspects of the present invention will now be illustrated in further detail, by way of example only.

EXAMPLE 1

Field Trials in Bangladesh

Lures were prepared from heat-sealed low density polyethylene sachets formed from 'layflat plastic' tubing. In early field work, the lures were prepared on site, with each lure comprising a single compound in a dose of 0.1 ml. The release rate of compounds from the polyethylene sachets is independent of the amount of material in the sachet and so a particular dosage affects longevity only. Longevity, in turn, is dependent on ambient temperature, with an increase of 7-10° C. leading to a doubling of the release rate. Water traps were placed at crop height and trap catches were taken as a crude measure of attractiveness to the compounds. As the compounds mimic 'floral odours' generally, they were not expected to be species-specific in their effect.

During testing, different combinations of floral odours, together with *H. armigera* pheromone, were used as attractants. The chemicals were put inside sealed plastic sachets (10×5 cm) and the sachets were hung inside traps prepared from clear plastic pots (19 cm height, 15 cm dia.) with two triangular holes (12 cm base, 9 cm height) at opposite sides. The traps were set at 1 m height with an inter-trap distance of 10 m. Insects that were trapped by the lures were collected, identified and recorded at weekly intervals.

TABLE 1

Effect of increasing relative amount of minor components on catch of adult *H. armigera*

| Blend code | Limonene (µl) | Phenyl acetaldehyde | Methyl 2-methoxy benzoate (µl) | Linalool (µl) | Salicylaldehyde (µl) | *H. armigera* Catch |
|---|---|---|---|---|---|---|
| 1.1 | 0 | 150 | 0 | 0 | 0 | 9 |
| 1.2 | 3 | 150 | 5 | 5 | 5 | 18 |
| 1.3 | 7 | 150 | 15 | 15 | 15 | 17 |
| 1.4 | 15 | 150 | 30 | 30 | 30 | 28 |
| 1.5 | 30 | 150 | 60 | 60 | 60 | 26 |
| 1.6 Pheromone | | | | | | 29 |

In Table 1, the importance of the minor components to the floral attractant composition for increasing attraction of *H. armigera* is illustrated. Trap catches doubled with the addition of 13% w/w (percentages are given with respect to phenylacetaldehyde) of the minor components (blend 1.2) compared with phenylacetaldyde alone (blend 1.1), and the catch continued to increase as the proportion of minor components was increased up to 70% w/w of phenylacetaldehyde (blend 1.4) beyond which (140% w/w of phenylacetaldehyde) the catch leveled out (blend 1.5). In addition, the total catch from the floral blends containing 70 and 140% w/w of minor components yielded comparable catches to the pheromone-containing lure (blend 1.6). A limitation of this trial is that it provides no indication of which of the minor components is responsible for the increase in catch. The trial did, however, provide a standard composition (blend 1.4; in bold) with which other blend combinations can be compared.

TABLE 2

Effect of removing single components from total blend on catch of adult *H. armigera*

| Blend code | Limonene (µl) | Phenyl acetaldehyde | Methyl 2-methoxy benzoate (µl) | Linalool (µl) | Salicylaldehyde (µl) | *H. armigera* Catch |
|---|---|---|---|---|---|---|
| 2.1 | 15 | 150 | 30 | 30 | 30 | 13 |
| 2.2 | 0 | 150 | 30 | 30 | 30 | 19 |
| 2.3 | 15 | 150 | 0 | 30 | 30 | 14 |
| 2.4 | 15 | 150 | 30 | 0 | 30 | 9 |
| 2.5 | 15 | 150 | 30 | 30 | 0 | 12 |
| 2.6 | 0 | 150 | 30 | 0 | 0 | 5 |
| Pheromone | | | | | | 22 |

In order to try to ascertain which of the minor components contributed to the increased catch, moth catches generated using the standard blend (blend 2.1) were compared with catches using blends in which a single minor component had been removed (Table 2). At the dose tested, removal of limonene appeared to increase catch (blend 2.2), which suggests that it might have an inhibitory effect. The other composition blends displayed similar overall catches.

TABLE 3

Averaged moth catch in lablab bean using traps baited with the standard floral odour-bait (blend 2.1)

| | *H. armigera* pheromones | Floral odour bait |
|---|---|---|
| Male *H. armigera* | 2.8 | 4.4 |
| Female *H. armigera* | 0 | 5.2 |
| *Maruca vitrata* | 0 | 6.6 |

The standard floral blend (blend 2.1) was found to catch almost twice as many male *H. armigera* as the standard sex pheromone lure (1 mg dose). Blend 2.1 also caught a significant number of female *H. armigera*. Interestingly, significant numbers of a related pest species *Maruca vitrata* (Lepidoptera: Pyralidae) were also trapped, suggesting that the floral blend might be useful for catching a range of pest species.

In Table 4, the results of tests to optimize the effective dose of salicylaldehyde are provided. The tests utilized the standard blend (blend 2.1, in bold), to which differing amounts of salicylaldehyde were added. The averaged trap catch data suggests that, as the quantity of salicylaldehyde is increased, so the total catch of *H. armigera* increases with no apparent upper limit to catch, even at the highest dose of salicylaldehyde tested (210 µL, blend 4.5). Interestingly, all of the tested blend compositions caught male and female moths in an approximate ratio of 1:3, and all floral blend compositions caught significantly more male moths than the standard sex pheromone.

TABLE 4

Averaged moth catch in a cotton crop using traps baited with different quantities of salicylaldehyde in the standard floral odour-bait (blend 2.1)

| Blend code | Standard blend less salicylaldehyde (µl) | Salicylaldehyde (µl) | *H. armigera* Average catch Male | *H. armigera* Average catch Female | Ratio f/m |
|---|---|---|---|---|---|
| 4.1 | 225 | 0 | 1.42 | 3.99 | 2.80 |
| 4.2 | 225 | 30 | 1.59 | 4.19 | 2.64 |
| 4.3 | 225 | 60 | 1.79 | 5.29 | 2.95 |
| 4.4 | 225 | 150 | 1.63 | 5.05 | 3.10 |
| 4.5 | 225 | 210 | 1.87 | 5.49 | 2.93 |
| Pheromone | | | 0.42 | 0 | |

In a similar trial to the one illustrated in Table 4, the standard blend composition (blend 2.1) with phenylacetaldehyde omitted (Table 5), was compared to blend compositions in which different quantities of phenylacetaldehyde were added. Again, the catch of both male and female *H. armigera* increased with dose of phenylacetaldehyde with no apparent levelling of catch with increased dose. In trial 5, all floral-odour blends tested caught more male *H. armigera* than were caught by the sex pheromone, with the ratio of male to female moths trapped being typically 1:3.

TABLE 5

Averaged moth catch in a cotton crop using traps baited with different quantities of phenylacetaldehyde in the standard floral odour-bait (blend 2.1)

| Blend code | Standard blend less Phenylacet-aldehyde (µl) | Phenylacet-aldehyde (µl) | *H. armigera* Average catch | | Ratio f/m |
|---|---|---|---|---|---|
| | | | Male | Female | |
| 5.1 | 105 | 0 | 0.61 | 1.70 | 2.78 |
| 5.2 | 105 | 30 | 0.87 | 2.69 | 3.09 |
| 5.3 | 105 | 60 | 1.02 | 3.78 | 3.72 |
| 5.4 | 105 | 150 | 1.38 | 4.35 | 3.15 |
| 5.5 | 105 | 210 | 1.67 | 5.45 | 3.27 |
| Pheromone | | | 0.42 | 0 | |

Phenylacetaldehyde is generally considered to be attractive to a wide range of Noctuidae and Pyralidae and although, in the above trials, it led to the capture of *H. armigera*, the numbers were low. A significant number of Hymenoptera were caught in the traps in addition to the moths. Accordingly, in one embodiment of the present invention, suitable deterrent compositions may be added to the attractant compositions, such as peppermint, tea tree oil, cinnamon, bitter almond, lemon oil, vanilla or citronella.

This research has produced an attractant that catches more female moths than the sex pheromone catches male moths, suggesting that the attractant can be used as the basis of a control strategy. Importantly, the attractant was effective at catching male and female *H. armigera* in a range of crops (cotton, lablab bean and chickpea) in the flowering stage, suggesting that attraction is unaffected by the background crop odour. The attractant also appears to be attractive to a range of other Noctuid pest species in these crops and recent research conducted in the UK has confirmed that the odour bait is attractive to the Silver-Y moth, *Autographa gamma*, which is an economically important migratory pest species of high-value leafy salads.

The odour-bait is composed of compounds found in a range of *H. armigera* host plants. Preliminary results show that the blend is attractive to both male and female moths and it is therefore assumed to act as a cue identifying a food (nectar) source. However, more female than male moths were caught in baited traps suggesting that the odour-bait may also provide the moths with information about the suitability of the source for oviposition.

The current research has identified a blend of five compounds, including phenylacetaldehyde and salicylaldehyde, which is a particularly effective attractant. Changes in the relative proportions of phenylacetaldehyde and salicylaldehyde appear to have a profound effect on attraction rates. Phenylacetaldehyde is present in current commercial products for trapping *Helicoverpa* (Magnet®, for example). It is also a minor component of a *Helicoverpa* attractant, which comprises salicylaldehyde, produced by Li et al. (2005).

In Europe and other temperate regions, the described odour-bait may have three functions: early season monitoring of pest populations, which is particularly important for migratory species such as *A. gamma*; assessment of the effectiveness of conventional control strategies; and control of pest populations, notably in protected crops, such as tomato, which is protected in Spain. In tropical regions, the odour-bait would have considerable commercial potential for use with field crops, notably chickpea, lablab bean and tomato.

In summary, the field trials of Example 1, conducted with cotton, tomato, chickpea and lablab bean, have generated an effective bait for *H. armigera*. The bait has also been shown to be attractive to *A. gamma* in the UK and *Maruca vitrata* in Bangladesh.

EXAMPLE 2

Field Trials in India and Bangladesh

Table 6 describes the floral bait traps utilised in three series of trials. In addition, five pheromone baited traps (baited with the pheromone of the key *Helicoverpa* and related spp.) were used as standards for each target species. Lures were changed every two to three weeks.

TABLE 6

2009-10 Floral bait trials composition

| | | Treatments | Replicates | Traps | Total traps per trial |
|---|---|---|---|---|---|
| Series 1 | Trial 1 | 9 | 3 | 27 | |
| Series 1 | Trial 2 | 4 | 4 | 16 | |
| Series 1 | Trial 3 | 10 | 3 | 30 | 73 |
| Series 2 | Trial 4 | 13 | 3 | 39 | |
| Series 2 | Trial 5 | 13 | 3 | 39 | 78 |
| Series 3 | Trial 6 | 10 | 3 | 30 | |
| Series 3 | Trial 7 | 10 | 3 | 30 | 60 |

The choice of pheromone trap depended on local availability. In India, the preferred trap was the standard Pheromone Chemicals Ltd. plastic funnel trap, while in Bangladesh a plastic water trap was used. Pheromone lures for the trials were provided by NRI. In India and Bangladesh, *H. armigera, Maruca vitrata, Earias vittella* and *Pectinophora gossypiella* lures were provided.

The floral baits were provided in sealed lay-flat polyethylene sachets. The sachets were hung inside the traps in the same way as the pheromone lures. Traps were supported at crop height and the height was adjusted periodically to account for crop growth. Yellow-coloured traps were avoided in order to deter pollinators. Preferably, traps should be colourless or green-coloured. Trap covers were opaque. Where necessary, a killing agent was incorporated into each trap—to ensure insects were dead before opening the trap to count catches.

Trial 1 was designed to investigate the effect of altering the relative amount of the two main components, phenylacetaldehyde and salicylaldehyde on catch. The trial was laid out in cotton fields at four locations: Narakoduru and Jammikunta in Andhra Pradesh, India, and Shreepur and Jessore in Bangladesh.

TABLE 7

Relative composition of lures used in Trial 1

| | Phenyl-acetaldehyde | Salicylal-dehyde | Methyl 2-methoxybenzoate | Linalool | Limonene |
|---|---|---|---|---|---|
| 96/01 | 0 | 100 | 0 | 0 | 0 |
| 96/02 | 3 | 97 | 0 | 0 | 0 |
| 96/03 | 10 | 90 | 0 | 0 | 0 |
| 96/04 | 30 | 70 | 0 | 0 | 0 |
| 96/05 | 50 | 50 | 0 | 0 | 0 |
| 96/06 | 70 | 30 | 0 | 0 | 0 |
| 96/07 | 90 | 10 | 0 | 0 | 0 |
| 96/08 | 97 | 3 | 0 | 0 | 0 |
| 96/09 | 100 | 0 | 0 | 0 | 0 |

*H. armigera* pheromone

Catches of *H. armigera* in traps with floral baits were low at both locations in India—compared with catches in traps baited with the sex pheromone. However, the opposite trend was found in the Bangladesh trials, where *H. armigera* catches in both Jessore and Shreepur exceeded those of the sex pheromone baited traps (Table 8).

TABLE 8

Total catches of *H. armigera* and other Lepidoptera from Trial 1

| Location | Narakoduru, Guntur | | Jammikunta KVK | | Shreepur | Jessore | Jessore |
| Crop | Cotton | | Cotton | | Cotton | Cotton | Country bean |
| Code | *H. armigera* | All Lepidoptera | *H. armigera* | All Lepidoptera | *H. armigera* | *H. armigera* | *H. armigera* |
|---|---|---|---|---|---|---|---|
| 96/01 | 0 | 8 | 0 | 3 | 1 | 16 | 3 |
| 96/02 | 1 | 28 | 2 | 11 | 6 | 25 | 2 |
| 96/03 | 1 | 37 | 3 | 20 | 8 | 23 | 1 |
| 96/04 | 2 | 56 | 1 | 15 | 25 | 24 | 0 |
| 96/05 | 2 | 75 | 1 | 17 | 19 | 32 | 1 |
| 96/06 | 3 | 86 | 1 | 13 | 35 | 31 | 3 |
| 96/07 | 0 | 75 | 1 | 21 | 27 | 30 | 2 |
| 96/08 | 4 | 100 | 0 | 4 | 26 | 42 | 3 |
| 96/09 | 1 | 94 | 1 | 15 | 20 | 30 | 0 |
| HA Pher | 701 | | 167 | | 8 | 33 | 2 |

In India, records were taken of all Lepidopterous species caught in the traps. The total Lepidoptera catches reflected the general trends in *H. armigera* catches. At all locations, blends 96/06 and 96/08 caught the highest number of Lepidoptera. Thus blends containing between 3 and 30 percent salicylaldehyde relative to phenylacetaldehyde were on average the most attractive of the binary blends tested.

In Trial 2, the standard 5-component blend used in Example 1 (96/12) was compared to: Magnet® (96/10), Li et al. (2005) (96/11) and a binary blend of phenylacetaldehyde and salicylaldehyde (96/13).

TABLE 9

Composition (ratio) of lures used in Trial 2 to compare the UoG standard blend with commercial standards.

| | Phenyl acetaldehyde | Salicyl aldehyde | Methyl 2-methoxybenzoate | Linalool | Limonene | Benzaldehyde | Benzyl alcohol | Phenylethyl alcohol | alpha pinene | anisyl alcohol | butyl salicylate | cineole |
|---|---|---|---|---|---|---|---|---|---|---|---|---|
| 96/10 | 1 | | | | 1 | | | | 1 | 1 | 1 | 1 |
| 96/11 | 3.4 | 46.1 | | | | 5.3 | 24.2 | 20.9 | | | | |
| 96/12 | 54.0 | 22.0 | 9.5 | 9.5 | 5.0 | | | | | | | |
| 96/13 | 70.5 | 29.5 | | | | | | | | | | |

*H. armigera* pheromone

In three of the four replicates of Trial 2, the 96/12 blend caught more moths than the 2-component blend and the blend developed by Li et al. (2005), apart from Jessore where catches were comparable. 96/12 caught similar numbers of moths to the commercial Magnet® blend of compounds (Table 10). In Bangladesh (Shreepur, Jessore), the blends caught similar numbers (or higher) of *H. armigera* as those caught by the female sex pheromone. In India (Narakoduru, Jammikunta), the sex pheromone caught significantly greater numbers of *H. armigera*—as for Trial 1.

TABLE 10

Total catches of *H. armigera* and Lepidoptera from Trial 2 comparison of standards

| Location | Narakoduru, Guntur | | Jammikunta KVK | | Shreepur | Jessore |
| Crop | Cotton | | Cotton | | Cotton | Cotton |
| Code | *H. armigera* | All Lepidoptera | *H. armigera* | All Lepidoptera | *H. armigera* | *H. armigera* |
| --- | --- | --- | --- | --- | --- | --- |
| 96/010 | 11 | 235 | 4 | 15 | 23 | 25 |
| 96/011 | 4 | 65 | 2 | 6 | 13 | 37 |
| 96/012 | 9 | 221 | 12 | 27 | 54 | 37 |
| 96/013 | 3 | 148 | 5 | 20 | 31 | 42 |
| HA Pher | 619 | | 25 | | 25 | 11.5 |

In Trial 3, a third component was added to a roughly 70:30 blend of phenylacetaldehyde:salicylaldehyde, to assess whether the additional compound made the binary blend more attractive to nocturnal Lepidoptera. The compositions of the blends tested are shown in Table 11 and the results in Table 12.

TABLE 11

Relative composition of lures used in Trial 3

| | Phenyl-acetaldehyde | Salicylal-dehyde | Methyl 2-methoxybenzoate | Linalool | Limonene |
| --- | --- | --- | --- | --- | --- |
| 96/14 | 70.5 | 29.5 | 0.0 | 0.0 | 0.0 |
| 96/15 | 69.3 | 27.7 | 3.0 | | |
| 96/16 | 64.3 | 25.7 | 10.0 | | |
| 96/17 | 50.0 | 20.0 | 30.0 | | |
| 96/18 | 69.3 | 27.7 | | 3.0 | |
| 96/19 | 64.3 | 25.7 | | 10.0 | |
| 96/20 | 50.0 | 20.0 | | 30.0 | |
| 96/21 | 69.3 | 27.7 | | | 3.0 |
| 96/22 | 64.3 | 25.7 | | | 10.0 |
| 96/23 | 50.0 | 20.0 | | | 30.0 |

*H. armigera* pheromone

Methyl 2-methoxybenzoate, linalool and limonene were added to a 70:30 blend of phenylacetadehyde:salicylaldehyde at 3, 10 and 30%. Addition of methyl 2-methoxybenzoate to the binary blend (96/14) increased moth catches at 30% for both *H. armigera* and other Lepidoptera, at all five locations tested (Table 12). However, there was no apparent increase in catch associated with addition of linalool and limonene at any of the doses tested. At 30%, limonene appeared to act as a repellent (96/23). In Bangladesh (Shreepur, Jessore), similar numbers of *H. armigera* were caught by the floral blends and by the female sex pheromone, while in India (Narakoduru, Jammikunta), the sex pheromone caught significantly larger numbers of *H. armigera*—as for Trials 1 and 2.

TABLE 12

Total catches of *H. armigera* and other Lepidoptera from Trial 3

| Location | Narakoduru, Guntur | | Jammikunta KVK | | Shreepur | Jessore | Jessore |
| Crop | Cotton | | Cotton | | Cotton | Cotton | Country bean |
| Code | *H. armigera* | All Lepidoptera | *H. armigera* | All Lepidoptera | *H. armigera* | *H. armigera* | *H. armigera* |
| --- | --- | --- | --- | --- | --- | --- | --- |
| 96/14 | 2 | 137 | 3 | 25 | 51 | 10 | 4 |
| 96/15 | 5 | 146 | 4 | 26 | 56 | 5 | 6 |
| 96/16 | 9 | 155 | 3 | 19 | 41 | 9 | 3 |
| 96/17 | 4 | 163 | 0 | 17 | 101 | 11 | 10 |
| 96/18 | 4 | 136 | 2 | 14 | 55 | 9 | 0 |
| 96/19 | 5 | 150 | 5 | 14 | 42 | 8 | 4 |
| 96/20 | 7 | 148 | 4 | 28 | 52 | 8 | 8 |
| 96/21 | 3 | 124 | 2 | 19 | 27 | 5 | 3 |
| 96/22 | 2 | 108 | 3 | 21 | 26 | 3 | 10 |
| 96/23 | 3 | 93 | 8 | 15 | 29 | 6 | 12 |
| HA Pher | 619 | | 143 | | 46 | 11.5 | 7 |

In Trial 4, two compounds were added to a 70:30 blend of phenylacetaldehyde:salicylaldehyde, to assess whether the additional compounds made the binary blend more attractive to nocturnal Lepidoptera. The compositions of the blends tested are shown in Table 13 and the results in Table 14.

TABLE 13

Relative composition of lures used in Trial 4

|       | Phenyl-acetaldehyde | Salicylal-dehyde | Methyl 2-methoxybenzoate | Linalool | Limonene |
|-------|---------------------|------------------|--------------------------|----------|----------|
| 96/24 | 70.5                | 29.5             | 0.0                      | 0.0      | 0.0      |
| 96/25 | 69.3                | 27.7             | 1.5                      | 1.5      |          |
| 96/26 | 64.3                | 25.7             | 5.0                      | 5.0      |          |
| 96/27 | 50.0                | 20.0             | 15.0                     | 15.0     |          |
| 96/28 | 69.3                | 27.7             |                          | 1.5      | 1.5      |
| 96/29 | 64.3                | 25.7             |                          | 5.0      | 5.0      |
| 96/30 | 50.0                | 20.0             |                          | 15.0     | 15.0     |
| 96/31 | 69.3                | 27.7             | 1.5                      |          | 1.5      |
| 96/32 | 64.3                | 25.7             | 5.0                      |          | 5.0      |
| 96/33 | 50.0                | 20.0             | 15.0                     |          | 15.0     |

*H. armigera* pheromone

Addition of a fourth component to the floral blend had a significant effect on catch of all Lepidoptera (Table 14). In each case, catches were increased compared with the binary blend (96/24) and, in particular, catches of *H. armigera* in India increased markedly compared to those obtained with the sex pheromone. In Bangladesh, catches of *H. armigera* with the floral blends exceeded those of the pheromone by a factor of ten. However, from the data, it is not possible to identify any one blend that caught significantly more moths at all locations tested.

TABLE 15

Relative composition of lures used in Trial 5

|       | Phenyl-acetaldehyde | Salicylal-dehyde | Methyl 2-methoxybenzoate | Linalool | Limonene |
|-------|---------------------|------------------|--------------------------|----------|----------|
| 96/34 | 70.5                | 29.5             | 0.0                      | 0.0      | 0.0      |
| 96/35 | 69.3                | 27.7             | 1.0                      | 1.0      | 1.0      |
| 96/36 | 65.0                | 26.0             | 3.0                      | 3.0      | 3.0      |
| 96/37 | 50.0                | 20.0             | 10.0                     | 10.0     | 10.0     |
| 96/38 | 7.1                 | 2.9              | 30.0                     | 30.0     | 30.0     |
| 96/39 | 69.6                | 27.9             | 1.0                      | 1.0      | 0.5      |
| 96/40 | 66.1                | 26.4             | 3.0                      | 3.0      | 1.5      |
| 96/41 | 53.6                | 21.4             | 10.0                     | 10.0     | 5.0      |
| 96/42 | 17.9                | 7.1              | 30.0                     | 30.0     | 15.0     |

*H. armigera* pheromone

In general, the addition of methyl 2-methoxybenzoate, linalool and limonene in either a 1:1:1 or 1:1:0.5 ratio at between 3 and 30% w/w levels increased catch of all Lepidoptera at each of the four locations tested, compared with the binary blend (Table 16). For the first time in India, the floral blends gave a comparable catch to the sex pheromone of *H.*

TABLE 14

Total catches of *H. armigera* and other Lepidoptera from Trial 4

| Location | Narakoduru, Guntur | | Vejendla Guntur | | Jammikunta KVK | | Shreepur |
|----------|--------------------|--|------------------|--|-----------------|--|----------|
| Crop     | Cotton             | | Tomato           | | Cotton          | | Cotton   |
| Code     | *H. armigera*      | All Lepidoptera | *H. armigera* | All Lepidoptera | *H. armigera* | All Lepidoptera | *H. armigera* |
| 96/24    | 6   | 20  | 1  | 101 | 3   | 18 | 89  |
| 96/25    | 15  | 27  | 14 | 192 | 13  | 17 | 97  |
| 96/26    | 13  | 26  | 7  | 140 | 10  | 18 | 220 |
| 96/27    | 12  | 29  | 5  | 145 | 9   | 26 | 149 |
| 96/28    | 18  | 28  | 3  | 164 | 18  | 41 | 131 |
| 96/29    | 18  | 30  | 8  | 146 | 15  | 30 | 133 |
| 96/30    | 4   | 21  | 3  | 140 | 1   | 19 | 115 |
| 96/31    | 9   | 21  | 6  | 130 | 8   | 24 | 138 |
| 96/32    | 14  | 20  | 6  | 128 | 6   | 15 | 130 |
| 96/33    | 16  | 27  | 10 | 168 | 9   | 38 | 134 |
| HA Pher  | 49  |     |    | 127 | 139 |    | 12  |

In Trial 5, the three compounds, methyl 2-methoxybenzoate, linalool and limonene were added to the binary 70:30 blend of phenylacetaldehyde:salicylaldehyde in two ratios, 1:1:1 and 1:1:0.5 at 3, 9, 30 and 90% w/w of the binary blend, to assess whether the additional compounds made the binary blend more attractive to nocturnal Lepidoptera. The compositions of the blends tested are shown in Table 15 and the results in Table 16.

*armigera* at one location, Jammikunta, but this may be a reflection of the low population present at the time. The highest catches were obtained with blends 96/37 and 96/41, which contained a 25-30% w/w of the three minor components (methyl 2-methoxybenzoate, linalool and limonene), confirming that the standard blend was indeed the optimal blend of the five compounds both for the target species *H. armigera* and other Lepidoptera.

TABLE 16

Total catches of *H. armigera* and other Lepidoptera from Trial 5

| Location | Narakoduru, Guntur | | Vejendla Guntur | | Jammikunta KVK | | Shreepur |
|---|---|---|---|---|---|---|---|
| Crop | Cotton | | Tomato | | Cotton | | Cotton |
| Code | *H. armigera* | All Lepidoptera | *H. armigera* | All Lepidoptera | *H. armigera* | All Lepidoptera | *H. armigera* |
| 96/34 | 3 | 14 | 2 | 120 | 1 | 14 | 44 |
| 96/35 | 12 | 22 | 3 | 118 | 12 | 27 | 95 |
| 96/36 | 7 | 20 | 2 | 125 | 7 | 22 | 92 |
| 96/37 | 24 | 37 | 4 | 138 | 23 | 40 | 89 |
| 96/38 | 22 | 26 | 7 | 96 | 13 | 22 | 60 |
| 96/39 | 9 | 20 | 2 | 139 | 6 | 19 | 75 |
| 96/40 | 15 | 29 | 2 | 130 | 13 | 34 | 99 |
| 96/41 | 14 | 29 | 2 | 140 | 10 | 28 | 69 |
| 96/42 | 9 | 12 | 2 | 115 | 7 | 14 | 79 |
| HA Pher | 57 | | 165 | | 8 | | |

In Tables 17 to 23 the total catches of selected Lepidoptera, Hymenoptera (*Apis mellifera* and *Bombus* spp.) and Diptera are shown.

The highest catches of Lepidoptera, Hymenoptera and Diptera were obtained with binary blends that contained more than 50% phenylacetaldehyde (Table 17). Salicylaldehyde alone (96/01) was unattractive to these species of Lepidoptera, although it was attractive to *H. armigera*. In contrast, phenylacetaldehyde alone (96/09) was attractive to all species recorded, but the addition of salicylaldehyde had only a modest effect on catch, most notably on *D. indica*.

TABLE 17

Total catches of non-target Lepidoptera, Hymenoptera and Diptera from Trial 1

| Location | | | | | | | | | |
|---|---|---|---|---|---|---|---|---|---|
| Crop | Narakoduru, Warangal District, AP, India |||||||||
| | | | | | Cotton | | | | |
| Code | *Spodopt. litura* | *Diaphania indica* | *Autogr. gama* | *Parnara guttat.* | *Lampides boeticus* | Other Lepidop. | *Apis mellifera* | *Bombus* spp. | Diptera |
| 96/01 | 1 | 1 | 0 | 0 | 0 | 6 | 10 | 0 | 1 |
| 96/02 | 1 | 9 | 1 | 1 | 0 | 16 | 5 | 0 | 4 |
| 96/03 | 2 | 8 | 3 | 2 | 0 | 23 | 4 | 0 | 4 |
| 96/04 | 1 | 16 | 3 | 6 | 0 | 34 | 9 | 1 | 6 |
| 96/05 | 2 | 16 | 10 | 5 | 0 | 45 | 15 | 3 | 10 |
| 96/06 | 2 | 23 | 8 | 20 | 1 | 50 | 12 | 2 | 17 |
| 96/07 | 1 | 14 | 4 | 19 | 1 | 56 | 19 | 1 | 9 |
| 96/08 | 4 | 21 | 9 | 12 | 0 | 62 | 20 | 1 | 10 |
| 96/09 | 1 | 13 | 12 | 14 | 1 | 67 | 18 | 1 | 8 |

The five-component blend (96/12) caught more moths, Hymenoptera and Diptera than the binary blend (96/13) (Table 18). Diptera appeared to be more attracted to the two- and five-component blends, whereas *A. mellifera* was more attracted by the five-component blend (96/12) and Magnet® (96/10).

There was no apparent increase in catch for any of the 3-component blends tested in Trial 3 (Table 19), compared with the catch obtained using the 2-component 70:30 blend of phenylacetaldehyde:salicylaldehyde (96/14), except perhaps for the Diptera and 'other Lepidoptera' with the addition of methyl 2-methoxybenzoate.

TABLE 18

Total catches of non-target Lepidoptera, Hymenoptera and Diptera from Trial 2

| Location | | | | | | | | | |
|---|---|---|---|---|---|---|---|---|---|
| Crop | Narakoduru, Warangal District, AP, India |||||||||
| | | | | | Cotton | | | | |
| Code | *Spodopt. litura* | *Diaphania indica* | *Autogr. gama* | *Parnara guttat.* | *Lampides boeticus* | Other Lepidop. | *Apis mellifera* | *Bombus* spp. | Diptera |
| 96/10 | 9 | 129 | 5 | 3 | 0 | 81 | 46 | 0 | 6 |
| 96/11 | 3 | 15 | 8 | 4 | 0 | 35 | 34 | 0 | 3 |
| 96/12 | 11 | 67 | 28 | 38 | 4 | 106 | 47 | 1 | 19 |
| 96/13 | 7 | 46 | 11 | 20 | 2 | 81 | 33 | 4 | 14 |

TABLE 19

Total catches of non-target Lepidoptera, Hymenoptera and Diptera from Trial 3

Location: Narakoduru, Warangal District, AP, India
Crop: Cotton

| Code | Spodopt. litura | Diaphania indica | Autogr. gama | Parnara guttatus | Lampides boeticus | Other Lepidopt. | Apis mellifera | Bombus spp. | Diptera |
|---|---|---|---|---|---|---|---|---|---|
| 96/14 | 4 | 34 | 6 | 14 | 0 | 91 | 18 | 6 | 6 |
| 96/15 | 5 | 25 | 16 | 21 | 4 | 95 | 20 | 3 | 13 |
| 96/16 | 1 | 27 | 6 | 18 | 4 | 112 | 13 | 1 | 16 |
| 96/17 | 6 | 31 | 13 | 12 | 0 | 109 | 10 | 2 | 12 |
| 96/18 | 2 | 20 | 9 | 15 | 1 | 101 | 11 | 3 | 10 |
| 96/19 | 6 | 32 | 11 | 10 | 2 | 96 | 9 | 4 | 6 |
| 96/20 | 4 | 35 | 7 | 10 | 2 | 95 | 18 | 5 | 5 |
| 96/21 | 2 | 24 | 4 | 20 | 1 | 91 | 5 | 3 | 7 |
| 96/22 | 2 | 24 | 6 | 18 | 0 | 74 | 11 | 0 | 9 |
| 96/23 | 3 | 17 | 7 | 8 | 1 | 63 | 3 | 0 | 3 |

Addition of a fourth component to the 70:30 blend of phenylacetaldehyde:salicylaldehyde (96/14) had no effect on catches of 'other Lepidoptera', Hymenoptera or Diptera in the trial conducted in Narakoduru (Table 20), although the catches were low. In contrast, at Vejendla, where populations were higher, significant differences were observed in catches between the binary blend (96/24) and four-component blend for the nocturnal moth species, S. Litura, D. indica and A. gama and 'other Lepidoptera', but the four-component blend had no effect on catches of Hymenoptera or Diptera (Table 21).

As with Trial 4 (Tables 20 and 21), low catches observed at Narakoduru meant that there was no apparent increase in catch caused by the addition of methyl 2-methoxybenzoate, linalool and limonene to the binary 70:30 blend (96/34) for any of the Lepidoptera, Hymenoptera or Diptera species observed. However, in Vejendla, where populations were higher, the catch of S. Litura and D. indica was significantly increased by the addition of the 1:1:1 blend of methyl 2-methoxybenzoate, linalool and limonene while catches of 'other Lepidoptera' were increased by the addition of a 1:1:0.5 ratio of the minor components (Table 24).

TABLE 20

Total catches of non-target Lepidoptera, Hymenoptera and Diptera from Trial 4

Location: Narakoduru, Warangal District, AP, India
Crop: Tomato

| Code | Spodopt. litura | Maruca testulalis | Cnaphal. medinalis | Parnara guttatus | Lampides boeticus | Other Lepidopt. | Apis mellifera | Bombus spp. | Diptera |
|---|---|---|---|---|---|---|---|---|---|
| 96/24 | 2 | 6 | 6 | 0 | 0 | 15 | 6 | n/a | n/a |
| 96/25 | 3 | 3 | 6 | 0 | 2 | 12 | 4 | n/a | n/a |
| 96/26 | 1 | 7 | 5 | 0 | 2 | 9 | 7 | n/a | n/a |
| 96/27 | 3 | 4 | 9 | 0 | 2 | 14 | 3 | n/a | n/a |
| 96/28 | 2 | 2 | 6 | 0 | 2 | 22 | 1 | n/a | n/a |
| 96/29 | 3 | 5 | 3 | 0 | 1 | 11 | 2 | n/a | n/a |
| 96/30 | 6 | 6 | 5 | 0 | 1 | 20 | 5 | n/a | n/a |
| 96/31 | 4 | 2 | 6 | 0 | 1 | 10 | 6 | n/a | n/a |
| 96/32 | 1 | 0 | 4 | 0 | 1 | 8 | 2 | n/a | n/a |

HA Pher

TABLE 21

Total catches of non-target Lepidoptera, Hymenoptera and Diptera from Trial 4

Location: Vejendla, Guntur District, AP, India
Crop: Tomato

| Code | Spodopt. litura | Diaphania indica | Autogr. gama | Parnara guttatus | Lampides boeticus | Other Lepidopt. | Apis mellifera | Bombus spp. | Diptera |
|---|---|---|---|---|---|---|---|---|---|
| 96/24 | 20 | 3 | 3 | 24 | 0 | 74 | 0 | 2 | 12 |
| 96/25 | 46 | 6 | 1 | 7 | 3 | 125 | 3 | 1 | 6 |
| 96/26 | 34 | 5 | 7 | 7 | 0 | 87 | 2 | 3 | 15 |
| 96/27 | 27 | 8 | 3 | 8 | 1 | 102 | 4 | 4 | 9 |
| 96/28 | 31 | 12 | 4 | 15 | 0 | 114 | 0 | 6 | 10 |
| 96/29 | 32 | 8 | 0 | 13 | 1 | 98 | 1 | 3 | 12 |
| 96/30 | 39 | 2 | 2 | 5 | 0 | 94 | 2 | 3 | 9 |
| 96/31 | 26 | 4 | 2 | 13 | 0 | 92 | 1 | 5 | 3 |
| 96/32 | 31 | 7 | 5 | 13 | 2 | 79 | 1 | 1 | 6 |

HA Pher

TABLE 22

Total catches of non-target Lepidoptera, Hymenoptera and Diptera from Trial 5

| Location | Narakoduru, Warangal District, AP, India | | | | | | | | |
|---|---|---|---|---|---|---|---|---|---|
| Crop | Tomato | | | | | | | | |
| Code | Spodopt. litura | Maruca testulalis | Cnaphal. medinalis | Parnara guttatus | Lampides boeticus | Other Lepidopt. | Apis mellifera | Bombus spp. | Diptera |
| 96/34 | 2 | 7 | 2 | 1 | 7 | 6 | 6 | n/a | n/a |
| 96/35 | 2 | 4 | 4 | 2 | 3 | 10 | 4 | n/a | n/a |
| 96/36 | 1 | 7 | 5 | 1 | 4 | 13 | 7 | n/a | n/a |
| 96/37 | 5 | 4 | 4 | 0 | 0 | 14 | 3 | n/a | n/a |
| 96/38 | 2 | 2 | 0 | 0 | 3 | 10 | 1 | n/a | n/a |
| 96/39 | 2 | 4 | 5 | 0 | 2 | 15 | 2 | n/a | n/a |
| 96/40 | 2 | 6 | 6 | 0 | 2 | 11 | 5 | n/a | n/a |
| 96/41 | 3 | 3 | 9 | 1 | 1 | 13 | 6 | n/a | n/a |
| 96/42 |   | 3 | 0 | 0 | 0 | 7 | 2 | n/a | n/a |

HA Pher

TABLE 23

Total catches of non-target Lepidoptera, Hymenoptera and Diptera Trial 5

| Location | Vejendla, Guntur District, AP, India | | | | | | | | |
|---|---|---|---|---|---|---|---|---|---|
| Crop | Tomato | | | | | | | | |
| Code | Spodopt. litura | Diaphania indica | Autogr. gama | Parnara guttatus | Lampides boeticus | Other Lepidop. | Apis mellifera | Bombus spp. | Diptera |
| 96/34 | 23 | 5 | 1 | 14 | 2 | 89 | 1 | 2 | 3 |
| 96/35 | 15 | 18 | 1 | 12 | 1 | 81 | 3 | 0 | 5 |
| 96/36 | 27 | 15 | 2 | 3 | 1 | 79 | 0 | 2 | 6 |
| 96/37 | 34 | 20 | 2 | 16 | 1 | 78 | 1 | 1 | 3 |
| 96/38 | 14 | 12 | 2 | 0 | 1 | 61 | 0 | 0 | 4 |
| 96/39 | 29 | 6 | 4 | 6 | 0 | 98 | 4 | 3 | 8 |
| 96/40 | 15 | 7 | 7 | 8 | 0 | 99 | 1 | 2 | 4 |
| 96/41 | 36 | 6 | 3 | 11 | 1 | 93 | 0 | 4 | 6 |
| 96/42 | 19 | 10 | 2 | 2 | 2 | 82 | 0 | 5 | 9 |

HA Pher

In summary, the field trials conducted in India and Bangladesh with cotton, tomato and country bean suggest that a 50:20:10:10:10 blend of phenylacetaldehyde, salicylaldehyde, methyl 2-methoxybenzoate, linalool and limonene is a particularly-attractive blend. However, any blends of phenylacetaldehyde and salicylaldehyde with at least two of the three minor components methyl 2-methoxybenzoate, linalool and limonene in ratios of between 3 and 30% had similar levels of attraction.

The influence of dose was not tested in these trials. However, it is not anticipated that the optimal blend will change with dose, as the current blends were tested over at least four-week periods, during which time there were no apparent variations in overall catch levels. The general trends in relative catch of *H. armigera* were mirrored in the total catch of Lepidoptera suggesting that the floral attractant would be useful at trapping pests in a crop which had a species complex.

In India, in addition to *H. armigera*, significant numbers of other pest species were also caught with the floral-baited traps notably *Spodoptera litura* (armyworm), *Earias vittella* (spotted bollworm), *Diaphania indica* (cucumber moth), *Autographa gama* (silver-Y), *Maruca testulalis* (legume pod borer), *Cnaphalocrocis medinalis* (rice leafroller), and low numbers of minor pests such as *Parnara guttatus* (paddy skipper), and *Lampides boeticus* (long-tailed pea-blue). The catches of *S. Litura* and *E. Vittella* were perhaps not too surprising given that they are cotton pests but the other species were unexpected. *D. indica* is a major pest of cucurbits in export crops such as gherkins. *M. testulalis* is a major pest of legumes. *L. boeticus* is a minor pest of legumes. *P. guttatus* and *C. medinalis* are pests of rice. *A. gama* is a polyphagous pest, not recognised by farmers in India, which is increasingly important in Europe.

REFERENCES

Bruce, T. J. & Cork, A. (2001) Electrophysiological and behavioural responses of female *Helicoverpa armigera* to compounds identified in flowers of African Marigold, *Tagetes erecta*. Journal of Chemical Ecology, 27, 1119-1131.

Bünning, E. (1956). Endogenous rhythms in plants. *Annual Review of Plant Physiology*, 7, 71-90.

Chamberlain D. J., Brown N. J., Jones O. T. & Casagrande E. (2000) Field evaluation of a slow release pheromone formulation to control the American bollworm, *Helicoverpa armigera* (Lepidoptera: Noctuidae) in Pakistan. *Bulletin of Entomological Research*, 90, 183-190.

Dobson, H. E. M. (1994) Floral volatiles in insect biology, pp. 47-81, in E A. Bernay (ed.). Insect-plant Interactions, Vol. V, CRC Press, Boca Raton, Fla.

Gabel, B., Thiéry, D., Suchy, V., Marion-Poll, F., Hradsky, P. and Farkas, P. (1992) Floral volatiles of *Tancetum vulgare* L. attractive to *Lobesia botrana* Den. Et Schiff. Females. *Journal of Chemical Ecology*, 18, 693-701.

Heath, R. R., Landolt, P. J., Dueben, B. & Lenczewski, B. (1992) Identification of floral compounds of night-blooming jessamine to cabbage looper moths. *Environmental Entomology*, 21, 854-859.

Hess, D. (1983) Die Blüte. Ulmer, Stuttgart.

Honda, K., Omura, H. & Hayshi. (1998). Identification of floral volatiles from *Ligustrum japonicum* that stimulate flower-visiting by cabbage butterfly, *Pieris rapae. Journal of Chemical Ecology*, 24, 2167-2180.

Ilse, D. (1928). Über den Farbensinn der Tagfalter. *Z. Vergl Physiology*, 8, 658-692.

Li, W.-Z., Yuan, G.-H., Sheng, C.-F., & Guo, X.-R. (2005) Active compounds in *Populus nigra* L. Wilted leaves responsible for attracting *Helicoverpa armigera* (Hübner) (Lep., Noctuidae) and new agaropectin formulation. *Journal of Applied Entomology*, 129, 557-562.

Matile, P. & Altenburger, R. (1988) Rhythms of fragrance emission in flowers. *Planta*, 174, 242-247.

Miyakawa, M. (1976). Flower-visiting behaviour of the small white butterfly, *Pieris rapae crucivora* Boisduval, *Annotationes Zoologicae Japonenses*, 49, 261-273.

Naumann, C. M., Ockenfell, P., Schmitz, J. & Francke, W. (1991). Reaction of *Zygaena* moths to volatile compounds of *Knautia arvensis* (Lepidoptera: Zygaenidae). *Entomologia Generalis*, 15, 255-264.

Pawar, C S Srivastava, C P & Reed, W. 1993 Phenylacetaldehyde: an attractant for *Heliothis armigera*. International Chickpea Newsletter, 8, 27-28

Scherer, C. and Kolb, G. (1987a). Behavioral experiments on the visual processing of color stimuli in *Pieris brassicae* L. (Lepidoptera). *Journal of Comparative Physiology, A,* 160, 645-656.

Wiesenborn, W. D. & Baker, T. C. (1990). Upwind flight to cotton flowers by *Pectinophora gossypiella* (Lepidoptera: Gelechiidae). *Environmental Entomology*, 19, 490-493.

Witzgall, P., Kirsch, P. & Cork, A. (2010). Sex pheromones and their impact on pest management, *Journal of Chemical Ecology*, 36, 80-100.

Zhu, Y., Keaster, A. J. & Gehardt, K. O. (1993). Field observations on attractiveness of selected blooming plants to noctuid moths and electroantennogram responses of black cutworm (Lepidoptera: Noctuidae) moths to flower volatiles. *Environmental Entomology*, 22, 162-16

The invention claimed is:

1. An attractant composition for attracting insects of the moth families Noctuidae and Pyralidae or the species *Diaphania indica* insects, the composition comprising phenylacetaldehyde, salicylaldehyde and at least one of methyl-2-methoxybenzoate, linalool and limonene, wherein phenylacetaldehyde comprises between 40 and 90% of the total weight of the composition, and salicylaldehyde comprises between 3 and 60% of the total weight of the composition.

2. An attractant composition as claimed in claim 1 comprising at least two of: methyl-2-methoxybenzoate, linalool and limonene.

3. An attractant composition as claimed in claim 2 wherein at least two of: methyl-2-methoxybenzoate, linalool and limonene, each comprise between 3 and 30% of the total weight of the composition.

4. An attractant composition as claimed in claim 1 comprising phenylacetaldehyde, salicylaldehyde, methyl-2-methoxybenzoate, linalool and limonene.

5. An attractant composition as claimed in claim 4 wherein the ratio of phenylacetaldehyde:salicylaldehyde:methyl-2-methoxybenzoate:linalool:limonene is approximately 50:20:10:10:10.

6. An attractant composition as claimed in claim 1 further comprising at least one compound selected from the group comprising: benzaldehyde, benzyl alcohol, phenylethyl alcohol, anisyl alcohol, α-pinene, butyl salicylate (Z)-jasmone, methyl salicylate, diacetone (4-hydroxy-4-methyl-2-pentanone), (*E*)-myroxide, (Z)-b-ocimene, and (R)-(−)-piperitone.

7. An attractant composition as claimed in claim 1 wherein the composition further comprises an antioxidant.

8. An attractant composition as claimed in claim 7 wherein the antioxidant is at least one of: α-tocopherol, α-, β-, γ-, or δ-tocotrienol, and butylated hydroxytoluene.

9. An attractant composition as claimed in claim 7 wherein the antioxidant comprises between 10 and 100% w/w, based on the amount of phenylacetaldehyde.

10. An attractant composition as claimed in claim 1 further comprising at least one of: a UV screener and a UV absorber.

11. An attractant composition as claimed in claim 10 wherein the composition comprises carbon black as UV screener.

12. An attractant composition as claimed in claim 10 wherein the composition comprises a UV absorber selected from at least one of: o-hydroxybenzophenones and benzotriazoles.

13. An attractant composition as claimed in claim 1 further comprising at least one carotenoid.

14. An attractant composition as claimed in claim 13, wherein at least one carotenoid is vitamin A.

15. A method of attracting insects of the moth families Noctuidae and Pyralidae or the species *Diaphania indica* insects comprising providing an attractant composition as claimed in claim 1.

* * * * *